United States Patent
Wei et al.

(10) Patent No.: US 10,927,234 B2
(45) Date of Patent: Feb. 23, 2021

(54) PVC PLASTICIZERS AND METHODS FOR MAKING THEREOF

(71) Applicant: KRATON POLYMERS LLC, Houston, TX (US)

(72) Inventors: Xiangyun Wei, Houston, TX (US); Jos H. M. Lange, Almere (NL)

(73) Assignee: Kraton Polymers U.S. LLC, Houston, TX (US)

( * ) Notice: Subject to any disclaimer, the term of this patent is extended or adjusted under 35 U.S.C. 154(b) by 104 days.

(21) Appl. No.: 16/250,219

(22) Filed: Jan. 17, 2019

(65) Prior Publication Data

US 2019/0218367 A1 Jul. 18, 2019

Related U.S. Application Data

(60) Provisional application No. 62/618,126, filed on Jan. 17, 2018.

(51) Int. Cl.

| | | |
|---|---|---|
| *C08K 5/3462* | (2006.01) | |
| *C07D 243/08* | (2006.01) | |
| *C07D 295/182* | (2006.01) | |
| *C08F 14/06* | (2006.01) | |
| *C08K 5/3442* | (2006.01) | |
| *C07D 295/027* | (2006.01) | |
| *C08K 5/00* | (2006.01) | |

(52) U.S. Cl.
CPC .......... *C08K 5/3462* (2013.01); *C07D 243/08* (2013.01); *C07D 295/027* (2013.01); *C07D 295/182* (2013.01); *C08F 14/06* (2013.01); *C08K 5/3442* (2013.01); *C08K 5/0016* (2013.01)

(58) Field of Classification Search
CPC .......... C08K 5/3462; C07D 243/08; C07D 295/182; C08F 14/06
USPC .......... 524/100
See application file for complete search history.

(56) References Cited

U.S. PATENT DOCUMENTS

| | | |
|---|---|---|
| 2,339,056 A | 1/1944 | Craver et al. |
| 2,541,584 A | 2/1951 | Jacoby |
| 2,975,149 A | 3/1961 | Port et al. |
| 3,219,614 A | 11/1965 | Skau et al. |
| 3,219,664 A | 11/1965 | Magne et al. |
| 3,519,661 A | 7/1970 | Mod et al. |
| 5,948,881 A * | 9/1999 | Shah .................. C08G 59/5026 524/100 |
| 7,411,012 B2 | 8/2008 | Kaytan |
| 8,093,319 B2 | 1/2012 | Hinault et al. |
| 2017/0190935 A1 | 7/2017 | Schaapman et al. |

FOREIGN PATENT DOCUMENTS

| | | |
|---|---|---|
| EP | 965627 A1 * | 12/1999 |
| WO | 2011/044018 A1 | 4/2011 |
| WO | 2016/115257 A2 | 7/2016 |

* cited by examiner

*Primary Examiner* — Hui H Chin

(57) ABSTRACT

A plasticized PVC composition free of phthalate is disclosed. The composition comprises a tertiary diamide plasticizer prepared from biorenewable feedstock such as fatty acid selected from tall oil fatty acids, tall oil fatty acid monomers, fatty acids derived from tall oil fatty acid, and mixtures thereof. The tertiary diamide plasticizer is a reaction product of a reactant mixture comprising the fatty acid and one or more monocyclic diamines.

19 Claims, No Drawings

PVC PLASTICIZERS AND METHODS FOR MAKING THEREOF

RELATED APPLICATIONS

This application claims priority from U.S. Application No. 62/618,126, with a filing date of Jan. 17, 2018, the disclosures of which is incorporated herein by reference.

FIELD

The present disclosure relates generally to a PVC plasticizer composition having a reduced carbon footprint, comprising tall oil based products, and methods for making thereof.

BACKGROUND

Plasticizers are added to materials to modify their physical properties, increase the plasticity, i.e., a non-reversible deformation of a material in response to an applied force, or to increase the fluidity. Commercial plasticizers are typically based on non-renewable petrochemical chemical feedstocks, like (tere)phthalic acid or benzoic acid.

In some widely used prior art plasticizers, e.g., DEHP (bis(2-ethylhexyl) phthalate), with molecular weight (MW) of 390.6 g/mol, the composition has good plasticizing efficiency, but migration rate is too high to be used in high temperature applications. Plasticizers are commonly divided into phthalate and non-phthalate plasticizers. In the petrochemical based, non-phthalate plasticizer, TOTM (trioctyl trimellitate), with MW of 546.8 g/mol, the composition has a relatively low migration rate suitable for high temperature applications, but it has poorer plasticizing efficiency.

Other petrochemical based non-phthalate plasticizers are known such as adipates, and trimellitates. In addition, cyclic monoamides have been described as plasticizers such as plasticizers derived from pyrrolidone. Several classes of bio-plasticizers have been developed, like sebacates, citrates, succinates, isosorbides, and plasticizers derived from castor oil, epoxidized soybean oil, etc. These bio-plasticizers are esters and generally do not offer optimal PVC compatibility and/or can exhibit unfavorable leakage-by-diffusion properties.

There is a still a need for a plasticized PVC polymer composition free of phthalate with improved properties, with balanced good plasticizing efficiency and low migration properties, which composition is based on a non-phthalate based and bio-renewable plasticizer component that helps in reducing carbon footprints.

SUMMARY

In one aspect, the disclosure provides a tertiary diamide composition for use as a plasticizer. The tertiary diamide composition is a reaction product of a mixture comprising: a tall oil fatty acid (TOFA) distillate selected from tall oil fatty acids, tall oil fatty acid monomers and other fatty acids derived from tall oil fatty acid; and one or more monocyclic diamines of Formula (1),

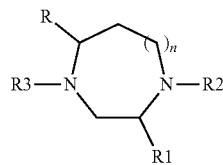

wherein R represents a hydrogen atom or methyl group, R1 represents a hydrogen atom or methyl group, n can have the value zero or one, and wherein R2 and R3 represent a hydrogen atom. In one embodiment, n has a value of zero in Formula (1).

In one aspect, the fatty acid distillate is derived from tall oil fatty acid with more than 80 wt. % of C18 carboxylic acids.

In one aspect, the tertiary diamide composition comprises at least one optionally ring-substituted piperazine or homopiperazine based diamide, having an eighteen carbon atom containing acyl group as present in TOFA or chemically modified TOFA.

In yet another aspect, the TOFA distillate is selected from isooleic acids, TOFA monomer, and branched saturated carboxylic acids.

DESCRIPTION

The following terms will be used throughout the specification and will have the following meanings unless otherwise indicated.

"Free of phthalate" means no phthalate is intentionally added.

"Carbon footprint" refers to the total greenhouse gas emission caused directly and indirectly by a product, process, or event. Carbon footprint can be measured in tonnes of carbon oxide equivalent.

"Low carbon footprint" or "reduced carbon footprint" means having <95%, or <92%, or <90%, or <80%, or <70%, or <50%, or <30% of the carbon footprint of a substitute product, process, or event. A tall oil fatty acid (TOFA) has a reduced carbon footprint, as depending on the sources, as compared to alternatives, e.g., TOFA may have 10% of emissions compared to a substitute soybean oil (https://www.forchem.com/forchem/low_carbon_solutions), or at least five times lower than a vegetable oil substitute made from soybeans, sunflowers, rapeseed and oleic mixtures (see http://www.kraton.com/products/pdf/Oleochemicals_web_final.pdf).

"Exudation" is used in the context of a plasticizer component included in a polymer composition, particularly a PVC composition. The term means a measure of the compatibility of a plasticizer component with a polymer matrix, such as, for example, PVC. Exudation of a plasticizer can be evaluated by placing a film sample between two pieces of tissue paper. The combined system (sample+paper) is then stored at room temperature for 48 hrs. The increase in weight of the paper after this duration gives a measure of the exudation of the plasticizer.

In one embodiment, this disclosure relates to a plasticizer composition based on bio-renewable feedstock, comprising a tall oil distillate-based diamide, with a balanced plasticizing efficiency and migration, wherein the molecular weight (MW) is optimized to shift the balance between plasticizing efficiency and migration rate. An amide group has higher polarity than an ester group, allowing incorporation of longer hydrocarbon chains, for good compatibility with PVC and a higher MW. In one embodiment, the diamide is made by reacting a tall oil fatty acid (TOFA) with any of diamines, polyamines, or mixtures thereof, for low migration rate and good plasticizing efficiency.

Tall Oil Fatty Acid ("TOFA") Component:

In one embodiment, the TOFA component is a TOFA distillate having one or more of the carboxylic acids covalently attached by means of an amidation reaction to a diamine component of general Formula (1) as described below, wherein R2 and R3 each represent a hydrogen atom. In one embodiment, the TOFA component contains more than 80 wt. % of C18 carboxylic acids. The TOFA component is characterized as having a reduced footprint, i.e., a total carbon footprint of <95% of the total carbon footprint of a fatty acid obtained from a vegetable oil.

In one embodiment, the TOFA component comprises long carbon chain (C18) acid function of the carboxyl group (COOH), with unsaturation of one or more carbon-carbon double bonds and relatively low cloud point and pour point. Examples include saturated C18 chain length acyl groups (stearic acid), a fraction of di-unsaturated C18 chain length acyl groups (linoleic acid), a fraction of mono-unsaturated C18 chain length acyl groups (oleic acid), some tri-unsaturated C18 chain length acyl groups (alpha-linolenic acid), a minor fraction of saturated C16 chain length acyl groups (palmitic acid), and a minor fraction of saturated and unsaturated acyl groups having a chain length of more than 18 carbon atoms.

In one embodiment, the carboxylic acids include but are not limited to the carboxylic acids having a carbon chain length of 16-20, such as palmitic acid, stearic acid, oleic acid, linoleic acid, elaidic acid, alpha-linolenic acid, arachidic acid, 14-methylhexadecanoic acid, octadecadienoic acid, 11,14-ericosadienoic acid, cis-5,cis-11,cis-14-Ericosatrienoic acid, 8(9), 15-lsopimaradien-18-oic acid, 2α-[2'(m-lsopropylphenyl)ethyl]-1β, 3α-dimethylcyclohexanecarboxylic acid, 8(9), 15-Pimaradien-18-oic acid, 2β-[2'(m-lsopropylphenyl)ethyl]-1β/3α-dimethylcyclohexanecarboxylic acid, 8(14), 15-Pimaradien-18-oic acid, 7(8)/15-Pimaradien-18-oic acid, 8,13-Abietadien-18-oic acid, palustric acid, 7,15-lsopimaradien-18-oic acid, isopimaric acid, dihydroabietic acid, abietic acid, 8,11,13-Abietadien-18-oic acid, 8(14), 13(15)-Abietadien-18-oic acid.

In one embodiment, the TOFA component has an oleic acid (weight %) in the range of 25 to 55%, a linoleic acid (%) level in the range of 25 to 55%, a conjugated linoleic acid (%) level in the range of 1 to 15%, a sum of alpha-linolenic acid and pinolenic acid in the range of 1 to 15%, a saturated fatty acid level in the range of 1 to 4% as determined by the ACQM 022 test method, and optionally 0-15 wt. % of linolenic acid. In one embodiment, the TOFA has an average carbon footprint of less than 500 gram $CO_2$ equivalents per kg of the fatty acid, preferably less than 200 gram $CO_2$ equivalents per kg of the fatty acid. In one embodiment, the TOFA component contains 0.1-5% C20 resin acids. An example is SYLFAT™ 2LT, a TOFA product from Kraton Corp., with an oleic acid level of about 32%, a sum of conjugated linoleic acid and linoleic acid is 50%, alpha-linolenic acid level of about 12%, saturated fatty acids of about 2%, an acid number of about 197 mg KOH/g (AQCM 001), an iodine number of about 154 cg I/g ((AQCM 009)) and a pour point of about −15° C. (AQCM 060). Another TOFA product is SYLFAT™ FA1 with an acid number of about 194 mg KOH/g, an iodine number of about 125 cg I/g, and a color of about 4.5 Gardner (neat) (AQCM 002). Yet another product is SYLFAT™ FA2 with an acid number of about 196 mg KOH/g, an iodine number of about 125 cg I/g, and a color of about 3.0 Gardner (neat).

Tall oil distillate predominantly contains Tall Oil Fatty Acid (TOFA). TOFA can be obtained by refining of crude tall oil grades. TOFA is developed for several applications, including but not limited to applications requiring low temperature properties. The pour point of TOFA generally indicates the lowest temperature at which the composition can be pumped. In one embodiment, the TOFA distillate has a pour point (° C.) in the range of −35° C. to 30° C. as determined by ACQM 060 test method. In another embodiment, the TOFA distillate has a pour point (° C.) in the range of −25° C. to 15° C. In one embodiment, the TOFA component has a pour point of −15° C.

In one embodiment, the TOFA component is a tall oil fatty acid monomer. TOFA monomer is the monomeric fraction which is formed during the acidic clay catalyzed polymerization of TOFA. In this process, which is typically conducted at high temperatures, the olefinic fatty acids undergo a variety of chemical reactions, including isomerizations and intermolecular addition reactions, so as to form a mixture of dimerized and polymerized fatty acid as well as a unique mixture of monomeric fatty acids. The monomeric fatty acids fraction is separated from the polymerization product by separation methods such as distillation and is commonly known in the art as "monomer" or "monomer acid" or "monomer fatty acid," and will be referred to herein as tall oil fatty acid monomer (CAS Registry Number 68955-98-6).

Tall oil fatty acid monomer is typically a mixture of branched-, aromatic-, cyclic-, and straight-chain fatty acids, which may be saturated or unsaturated and wherein olefinic bonds can have cis- or trans-configuration. The predominant acid in tall oil fatty acid monomer is "iso-oleic acid", where iso-oleic acid is a mixture of linear, branched and cyclic C18 mono-unsaturated fatty acids. A commercially tall oil fatty acid monomer product is for example CENTURY™ D1 from Kraton Corp. which contains both saturated and unsaturated C-18 fatty acids. Branched chain iso-oleic acids constitute the main portion, with a low level of polyunsaturated fatty acids. CENTURY™ D1 has an acid number of about 174 mg KOH/g (AQCM 001), a Gardner color (neat) of about 6.1 (AQCM 002), and an iodine number of about 75 cg I/g ((AQCM 009)).

In another embodiment, the TOFA component is a chemically modified TOFA such as isooleic acid and their refined or hydrogenated fractions, e.g., isostearic acid and related branched saturated or partly saturated C18 carboxylic acid compositions. In one embodiment, the TOFA monomer is a mixture of branched and straight chain fatty acids which is formed during the dimerization reaction of TOFA and obtained from the resulting reaction mixture. In another embodiment, the TOFA monomer contains both saturated and unsaturated C18 fatty acids, with branched chain isooleic acids constituting the main portion and with virtually no polyunsaturated fatty acids.

Iodine number is generally used as a measure of the degree of unsaturation of an oil, fat, or wax. In one embodiment, the TOFA or TOFA monomer component has an iodine number in centigrams of iodine/gram of TOFA cg I/g ranging from 60 to 180 as determined by the ACQM 009 test method. In another embodiment, the iodine number of TOFA component ranges 110-170 cg I/g. In yet another embodiment, the iodine number of TOFA component ranges 125-155 cg I/g.

Diamine Component:

The diamine component is a cyclic diamine reactant of general Formula (1):

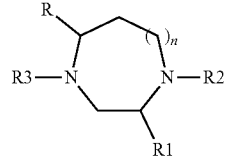

Formula (1)

where R is a hydrogen atom or methyl group, R1 is a hydrogen atom or methyl group, n has a value of zero or one, and R2 and R3 each represent a hydrogen atom.

The diamine component can be prepared according to synthetic methods known in the art. Examples include, but are not limited to, cyclizations of alkyldiamines or alkyldiamine-alcohol derivatives into cyclic diamines, or alkyl dihalogenides such as 1,3-bromopropane which are cyclized with (optionally N-protected) alkyldiamines, or alternatively they can be prepared from alkyldiamines which are cyclized with diols into cyclic amines of the general formula 1.

Optional Components:

In one embodiment, in addition to the TOFA and diamine components, the reaction mixture further comprises any of a rosin-containing material, e.g., a tall oil rosin, a gum rosin or a combination thereof, in an amount of less than 15% by weight (relative to the total weight of the diamide plasticizer). Examples include rosin-containing material under the SYLVAROS™ brand from Kraton Corporation.

Method for Making Diamides Plasticizer:

The tertiary diamides for use as plasticizer can be prepared by reacting one or more cyclic diamine reactants of general Formula (1) with a TOFA component, e.g., fatty acids selected from tall oil fatty acid, tall oil fatty acid monomer, isooleic acid, and saturated branched fatty acids, optionally in the presence of relatively small amount of rosin as a co-reactant, and optionally in the presence of an amidation catalyst known in the art.

Examples of amidation catalysts include but are not limited to phosphoric acid, hypophosporous acid, 2-(2'-Pyridyl) ethylphosphonic acid (PEPA) and its diethyl ester (DPEP), sodium hypophosphite, phenylphosphonic anhydride, phenylphosphinic acid, arylboronic acid and other boron containing chemical entities, Lewis acids like FeCl3, dehydrating agents such as molecular sieves, phosphonium salts and carbodiimides.

The amidation reaction is in generally conducted at elevated temperatures. Water is formed as a by-product during the amidation reaction and is preferably removed during the reaction as a vapor, for example via a stream of inert purge gas such as N2. An antioxidant, e.g., Irganox™ 1010 or Irganox™ 565, can be added during the reaction or at the end of the reaction in order to stabilize the diamide product against oxidative decomposition. Amides can also be synthesized from certain carboxylic acid derivatives and amines. An example is the synthesis of amides from esters and amines, preferably in the presence of a catalyst. Methyl esters or low alkyl esters are preferably applied herein. Alternatively, amides can be synthesized from acid chlorides ("acyl chlorides") and amines, preferably in the presence of a base. Alternatively, amides can be synthesized from acid anhydrides and amines.

In one embodiment, a diamide product is recovered, comprising at least one piperazine or homopiperazine (1,4-diazepane) based diamide having an eighteen carbon atom containing acyl group as present in tall oil or an acyl group as present in chemically modified tall oil composition, attached to each nitrogen atom. The acyl group in the diamide can be the same or different. In another embodiment, the diamide plasticizer comprises at least one optionally ring-substituted piperazine or homopiperazine based diamides having an eighteen carbon atom containing acyl group as present in tall oil, or an acyl group as present in chemically modified tall oil compositions attached to each nitrogen atom, which acyl group can be the same or different.

Properties of the Diamide Plasticizer:

The tall oil based diamide plasticizer does not leak, and has a low tendency to exudation. The plasticizer can be used in compositions comprising PVC and/or vinyl chloride-vinyl acetate copolymer resin, also known as Vinylite (VYDR). The plasticizer is characterized as being substantially compatible to PVC and/or Vinylite VYDR Resin. Because of the source of the raw material as a reactant, i.e., a fatty acid selected from tall oil fatty acids, tall oil fatty acid monomers, fatty acids derived from tall oil fatty acid, the diamide plasticizer is characterized as having a reduced carbon footprint, with a carbon footprint of less than about 95% of a comparable plasticizer made from products other than tall oil fatty acid, e.g., vegetable oil.

The diamide plasticizer is characterized by a third moment or third power average molecular weight Mz of less than 1800, or less than 1300, or less than 1000.

The diamide plasticizer is characterized by an acid number of less than 12 mg KOH/g in one embodiment; less than 9 mg KOH/g in a second embodiment, and less than 5 mg KOH/g in a third embodiment.

The diamide plasticizer is further characterized by an amine value of less than 6 mg KOH/g in one embodiment; less than 4 mg KOH/g in a second embodiment, and less than 1 mg KOH/g in a third embodiment.

Industrial Applicability:

The tall oil based diamide plasticizer can be used in compositions for use in construction applications, e.g., pipe and profile applications such as doors and windows. It can also be used in compositions for use in making bottles, non-food packaging, and cards (such as bank or membership cards). Other applications include plumbing, electrical cable insulation, imitation leather, signage, phonograph records, flooring, inflatable products, toys, and many applications where it replaces rubber. In one embodiment, the plasticizer is incorporated into compositions for use in surface floorings, e.g., decorative surface coverings, floor coverings, underlay/overlay flooring, in compositions comprising 15-40 wt. % of a polymer such as PVC, from 4 to 15 wt. % of the diamide plasticizer, from 40 to 80 wt. % filler, and optional additives such as stabilizers.

In embodiments, the tall oil based diamide plasticizer is used in applications including PVC films, electric wire coating applications, insulation coating materials, engineered planks for floor covering, floor tiles, floor panels, artificial leather materials, sheets, cable jackets, fuel tubings, medical tubings, components of adhesives, adhesive sealants, sealing compositions, paints, inks, foamed surface coverings, artificial leather for vehicle manufacture, underbody protection for vehicles, joint seals, carpet backing coatings, heavy duty coatings, conveyor belts, dip coatings, housing of electrical appliances, such as for example kitchen appliances and computer housings, tools, pipes, cables, hoses, such as for example plastic hoses, watering and irrigation hoses, industrial rubber hoses or chemical hoses, wire sheathings, window profiles, components for automobile construction, such as for example bodywork components, vibration dampers for engines, tires, furniture, such as for example chairs, tables or shelves, foam for pillow and mattresses, seals, composite films, such as films for composite safety glass, in particular for automobile windows and window panes, records, packaging containers, and adhesive tape films or coatings.

The diamide plasticizer can be incorporated into polymer compositions such as PVC by methods including but not limited to plastisol method, dry blending, compounding, and extrusion. The optimum process of incorporating plasticizers into polymer depends on many variables, including but not limited to downstream process, desired property balance and intended applications. Dry blending is one of the common methods for incorporating plasticizers into polymer compositions, and it can be accomplished by using a ribbon blender, or a high speed mixture, or other mixing equipment. In one embodiment, the diamide plasticizer is incorporated in an amount ranging from 30-90 phr (parts by weight per 100 parts by weight of the polymer). Appropriate amounts of polymer and solid ingredients are blended together first, and liquid plasticizer is subsequently added while stirring. Brabender is then used to further process the dry blend at temperature between 175 to 205° C. The processed polymer compound is then compression molded, by using a hydraulic presser, into testing plaques. The compression molding temperature is between 350 and 400° F., and typical pressure is between 30,000 and 40,000 psi.

In embodiments, the diamide plasticizer is incorporated into a molding compound with a polymer, e.g., a thermoplastic polymer selected from polyvinyl chloride (PVC), polyvinyl butyral (PVB), homo- and copolymers of vinyl acetate, homo- and copolymers of styrene, polyacrylates, thermoplastic polyurethanes (TPU) or polysulfides, in an amount from 1.0 to 300 phr. In embodiments, the polymer is an elastomer.

EXAMPLES

The following illustrative examples are intended to be non-limiting. The following tests can be used to measure properties in the Example.

Viscosity can be determined according to ASTM D2196 with spindle No. 21.

Acid number refers to acid value (or "neutralization number" or "acid number" or "acidity") determined by ASTM D465-05 (2010), which is mass of potassium hydroxide (KOH) in milligrams required to neutralize one gram of chemical substance.

Amine value (or "amine number") of diamides is milligrams of potassium hydroxide (KOH) equivalent to the basicity in 1 gram of sample, titrated with diluted hydrochloric acid in isopropanol as solvent, with colorimetric end-point determination.

Glass transition temperature (Tg) values of diamides can be determined by Differential Scanning calorimetry (DSC) and expressed in oC.

Tensile & elongation: Per ASTM D882-12.

Hardness: Per ASTM D2240-15.

Yellowness index (YI): Per ASTM E313-15e1.

The third moment or third power average molecular weight ($M_z$) is a higher order molecular weight average which can be calculated according to Equation 1:

$$M_z = \frac{\Sigma_i N_i M_i^3}{\Sigma_i N_i M_i^2}$$

Equation (1), where $N_i$ is the amount of substance of species i, and $M_i$ is the MW of species i.

Mw or weight average MW can be determined by gel permeation chromatography, and calculated according to Equation 2:

$$M_w = \frac{\Sigma_i N_i M_i^2}{\Sigma_i N_i M_i}$$

Equation (2), where $N_i$ is the amount of substance of species i and $M_i$ is the MW of species i.

Mn or number average MW (Mn) can be determined by gel permeation chromatography, and calculated according to Equation 3:

$$M_n = \frac{\Sigma_i N_i M_i}{\Sigma_i N_i}$$

Equation (3), where $N_i$ is the amount of substance of species i and $M_i$ is the MW of species i.

Example 1

SYLFAT™ FA2 from Kraton Corporation (549.4 grams, acid value 199.9 mg KOH/g) is charged into a 1 liter four neck round bottom flask along with 60.8 grams of SYLVAROS™ HYR tall oil rosin, also from Kraton, and 0.02 grams of phosphoric acid. The mixture is stirred while heating to 90° C. under a nitrogen atmosphere. Piperazine (89.7 grams) is added and the resulting mixture is heated to 150° C. At 150° C., the reaction is heated up to 170° C., allowing for the water of reaction to be removed. Once at a temperature of 170° C., the reaction is heated with 15° C./hr up to 200° C., and subsequently with 30° C./hr up to 270° C. The reaction is held at 270° C. for seven hours, subsequently cools to 190° C. for the addition of 3.5 g Irganox™ 1010 antioxidant and poured into a storage vessel.

The resulting properties include: Gardner color (neat) 12, acid value 4.7 mg KOH/g, amine value 0.4 mg KOH/g and a viscosity 319 cPs at 30° C. The final product is analyzed using GPC as well as DSC, showing Mz 1223 g/mol, Mn 864 g/mol, Mw 1015 g/mol, and Tg 5.8° C.

Example 2

Tall oil fatty acid SYLFAT™ FA2 (1213.2 grams) is charged and stirred into a 3 liter four neck round bottom flask while heating to 80° C. under a nitrogen atmosphere. Piperazine (186.7 grams) is added and the resulting mixture heated to 160° C. At 160° C., the reaction is heated up to 190° C. allowing for the water of reaction to be removed. At 190° C., the reaction mixture is heated with 30° C./hr up to 220° C. At 220° C., 0.02 grams of phosphoric acid is added. The reaction is held at 220° C. for 12 hours and subsequently cooled to 100° C. and poured into a storage vessel. The mixture is stripped using a N2 purge for 7.5 hours. The resulting properties include: Gardner color (neat) 9.2, acid value 4.1 mg KOH/g, amine value 1.1 mg KOH/g, viscosity 154 cPs (30° C.), Mz 936 g/mol, Mn 852 g/mol, Mw 905 g/mol, and Tg 11.1° C.

Example 3 (Comparative)

Technical grade 90% oleic acid (602.4 grams, Gardner color (neat) 0.1, Acid value 202 mg KOH/g) is charged into a 1 liter four neck round bottom flask and stirred while heating to 80° C. under a nitrogen atmosphere. Piperazine (97.6 grams) is added and the mixture was heated to 160° C. At 160° C. the reaction is heated up to 190° C. allowing for the water of reaction to be removed. At 190° C., the reaction mixture is heated with 30° C./hr up to 220° C., at which 0.02 g of phosphoric acid is added. The reaction is held at 220° C. for 5 hours and poured into a storage vessel. The resulting properties include: Gardner color (neat) 4.8, acid value 4.4 mg KOH/g, amine value 1.3 mg KOH/g, Mz 930 g/mol, Mn 905 g/mol, and Mw 918 g/mol.

Examples 4-11

General procedure as applied in Examples 4-11: Tall oil fatty acid or tall oil fatty acid Monomer (CENTURY™ D1) and catalyst are charged into an addition funnel and assembled to the reaction flask in which the anhydrous piperazine is charged. The reaction setup is purged with N2 for 30 min and the reactants in the addition funnel are slowly added to the reaction vessel. The mixture is stirred at 300 rpm and allowed to purge with N2 for 15 min and heated to 80° C. At 80° C. the reaction is heated up to 210° C., allowing for the water of reaction to be collected and removed from the system. The reaction is held at 210° C. for a total of 3 hours. The resulting reaction mixture is then stripped at 210° C. using a stream of N2 gas for a total of 2 hours and subsequently poured into a storage vessel. The yield of the chemical composition as synthesized in example 11 amounted to 1272 grams.

TABLE 1

Fatty acids, piperazine, and catalysts and their amounts as applied in Examples 4-11:

| Ex. | Fatty acid | Fatty Acid (g) | Piperazine Amount (g) | Catalyst(s) | Catalyst(s) Amount (g) |
|---|---|---|---|---|---|
| 4 | SYLFAT™ FA1 | 1213.2 | 186.9 | None | 0 |
| 5 | SYLFAT™ FA1 | 1212.9 | 187.0 | Phosphoric acid | 0.03 |
| 6 | SYLFAT™ FA1 | 1204.5 | 189.9 | Hypophosphorous acid + Phenylphosphonic acid | 2.84 + 4.22 |
| 7 | SYLFAT™ FA1 | 1199.0 | 193.9 | Hypophosphorous acid | 13.96 |
| 8 | SYLFAT™ FA1 | 1207.4 | 188.4 | Phenylphosphonic acid | 4.19 |
| 9 | SYLFAT™ FA2 | 1195.4 | 197.5 | Hypophosphorous acid | 14.20 |
| 10 | CENTURY™ D1 | 1214.7 | 178.4 | Hypophosphorous acid | 13.88 |
| 11 | TOFA | 1196.9 | 197.0 | Hypophosphorous acid | 14.02 |

Applied SYLFAT™ FA1 in examples 4-8: Gardner color (neat) 5.0, Acid Value 199.9 mg KOH/g. Applied SYLFAT™ FA2 in example 9: Gardner color (neat) 3.7, Acid Value 199.9 mg KOH/g. Applied CENTURY™ D1 in example 10: Gardner color (neat) 3.1, Acid Value 177 mg KOH/g. Applied TOFA grade in example 11: Gardner color neat 2.2, Acid Value 199.8 mg KOH/g. The hypophosphorous acid weight is given as the added weight of the applied 50 wt % aqueous H3PO2 solution.

TABLE 2

Properties of the chemical compositions as synthesized in examples 4-11.

| Example | Color (Gardner (neat)) | Acid Value (mg KOH/g) | Amine Value (mg KOH/g) |
|---|---|---|---|
| 4 | 8.1 | 10.9 | 5.6 |
| 5 | 7.9 | 9.5 | 4.1 |
| 6 | 5.8 | 7.5 | 1.8 |
| 7 | 4.7 | 5.8 | 2.9 |
| 8 | 9.1 | 9.0 | 0.9 |
| 9 | 3.0 | 3.0 | 0.3 |
| 10 | 4.9 | 4.8 | 0.4 |
| 11 | 2.0 | 3.0 | 1.2 |

Example 12

Various PVC formulations are prepared with different plasticizers in an amount of 60 phr, stabilizer such as Plastistab 2187 from AM Stabilizers Corp., or BAEROPAN MC 90249 KA/4 from Bareolocher in an amount of 5 phr, and anti-oxidant Irganox 1010 of 0.3 phr. The results are shown in Table 3:

TABLE 3

| Plasticizer (60 phr) | YI | Shore A Hardness | Tensile (psi) | Elongation (%) |
|---|---|---|---|---|
| DEHP (bis(2-ethylhexyl) phthalate) | 15 | 77.0 | 1,740 | 250% |
| TOTM (tris(2-ethylhexyl) trimellitate) | 12 | 84.0 | 2,493 | 254% |
| Diamide of Example 1 | 87 | 84.0 | 2,597 | 332% |
| Diamide of Example 2 | 70 | 81.6 | 2,243 | 332% |

Exudation Test:

In the exudation test, Plasticized PVC ("PPVC") films made from the Diamide of Examples 1-3 did not present any significant mass loss of PPVC samples during the experimental period (48 hrs, room temperature) as shown in Table 4. This can be attributed to the excellent compatibility of both the plasticizer components with PVC, for excellent plasticizing effect with little if any mass loss. Whereas, PPVC samples using plasticizers of the prior art, e.g., PPVC 4 and PPVC 5 showed leaching of plasticizer on the paper.

TABLE 4

| Sample | Initial sample weight (g) | % weight loss after 48 hrs |
|---|---|---|
| PPVC1 | 1.007 | 0 |
| PPVC2 | 1.038 | 0 |
| PPVC3 | 1.169 | 0 |
| PPVC4 | 1.151 | 3.1754 |
| PPVC5 | 1.014 | 7.2721 |

Unless defined otherwise, all technical and scientific terms used herein have the same meanings as commonly understood by one of skill in the art to which the disclosed disclosure belongs. Publications cited herein and the materials for which they are cited are specifically incorporated by reference. The term "comprising" and variations thereof as used herein is used synonymously with the term "including" and variations thereof and are open, non-limiting terms. Although the terms "comprising" and "including" have been used herein to describe various aspects, the terms "consisting essentially of" and "consisting of" can be used in place of "comprising" and "including" to provide for more specific aspects of the disclosure and are also disclosed.

For the purposes of this specification and appended claims, unless otherwise indicated, all numbers expressing quantities, percentages or proportions, and other numerical values used in the specification and claims, are to be understood as being modified in all instances by the term "about." Accordingly, unless indicated to the contrary, the numerical parameters set forth in the following specification and attached claims are approximations that can vary depending upon the desired properties sought to be obtained. It is noted that, as used in this specification and the appended claims, the singular forms "a," "an," and "the," include plural references unless expressly and unequivocally limited to one referent. As used herein, the term "include" and its grammatical variants are intended to be non-limiting, such that recitation of items in a list is not to the exclusion of other like items that can be substituted or added to the listed items. As used herein, the term "comprising" means including elements or steps that are identified following that term, but any such elements or steps are not exhaustive, and an embodiment can include other elements or steps.

Unless otherwise specified, the recitation of a genus of elements, materials or other components, from which an individual component or mixture of components can be selected, is intended to include all possible sub-generic combinations of the listed components and mixtures thereof.

The patentable scope is defined by the claims, and can include other examples that occur to those skilled in the art. Such other examples are intended to be within the scope of the claims if they have structural elements that do not differ from the literal language of the claims, or if they include equivalent structural elements with insubstantial differences from the literal languages of the claims. To an extent not inconsistent herewith, all citations referred to herein are hereby incorporated by reference.

The invention claimed is:

1. A tertiary diamide composition, comprising a reaction product of a reactant mixture consisting essentially of:
   a fatty acid selected from tall oil fatty acids, tall oil fatty acid monomers, fatty acids derived from tall oil fatty acid, and mixtures thereof; and
   one or more monocyclic diamines of Formula (1),

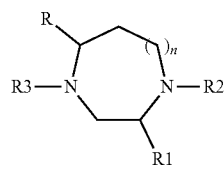

wherein R represents a hydrogen atom or methyl group, R1 represents a hydrogen atom or methyl group, n can have the value zero or one, and wherein R2 and R3 represent a hydrogen atom.

2. The tertiary diamide composition of claim 1, wherein the fatty acid contains more than 80 wt. % of C18 carboxylic acids.

3. The tertiary diamide composition of claim 1, wherein the fatty acid comprises 20-55 wt. % of oleic acid, 20-55 wt. % of linoleic acid, and optionally 0-15 wt. % of linolenic acid.

4. The tertiary diamide composition of claim 1, wherein the fatty acid has a total carbon footprint of <95% of the total carbon footprint of a fatty acid obtained from a vegetable oil.

5. The tertiary diamide composition of claim 1, wherein R, R1, R2 and R3 represent a hydrogen atom and n is zero.

6. The tertiary diamide composition of claim 1, wherein the reactant mixture further comprises at least a tall oil rosin, a gum rosin and mixtures thereof, in an amount of less than 15% by weight.

7. The tertiary diamide composition of claim 1, characterized as having an acid number of less than 12 mg KOH/g.

8. The tertiary diamide composition of claim 1, characterized as having an amine value of less than 6 mg KOH/g.

9. The tertiary diamide composition of claim 1, characterized as having a third power average molecular weight Mz of less than 1800.

10. The tertiary diamide composition of claim 1, wherein the fatty acid is a tall oil fatty acid.

11. The tertiary diamide composition of claim 1, wherein the fatty acid is isostearic acid comprising a mixture of branched and straight-chain saturated C18 fatty acids.

12. The tertiary diamide composition of claim 1, wherein the fatty acid is a tall oil fatty acid monomer.

13. The tertiary diamide composition of claim 1, wherein the fatty acid comprises saturated and unsaturated C-18 fatty acids, with branched chain isooleic acids constitute the main portion and with virtually no polyunsaturated fatty acids.

14. A molding compound comprising at least one polymer and the tertiary diamide composition of claim 1.

15. The polymer composition of claim 1, wherein the polymer is polyvinyl chloride.

16. A polymer composition comprising the tertiary diamide composition of claim 1 as a plasticizer.

17. A method of preparing a plasticized PVC composition free of phthalate, comprising blending and compounding the tertiary diamide composition of claim 1 with PVC and one or more polymer stabilizers and antioxidants.

18. The method of claim 17, wherein the plasticized PVC composition is characterized as having a weight loss after 48 hours of less than 1% in an exudation test.

19. A method of preparing a plasticizer composition free of phthalate, comprising mixing and heating a reactant mixture consisting essentially of:
   one or more fatty acid selected from tall oil fatty acids, tall oil fatty acid monomers, fatty acids derived from tall oil fatty acid, and mixtures thereof; and
   one or more monocyclic diamines of Formula (1),

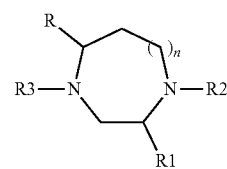

wherein R represents a hydrogen atom or methyl group, R1 represents a hydrogen atom or methyl group, n can have the value zero or one, and wherein R2 and R3 represent a hydrogen atom.

* * * * *